(12) United States Patent
Jung et al.

(10) Patent No.: US 12,385,037 B2
(45) Date of Patent: Aug. 12, 2025

(54) ENRICHMENT OF SHORT NUCLEIC ACID FRAGMENTS IN SEQUENCING LIBRARY PREPARATION

(71) Applicant: GRAIL, INC., Menlo Park, CA (US)

(72) Inventors: Byoungsok Jung, Atherton, CA (US); Alex Aravanis, San Mateo, CA (US)

(73) Assignee: GRAIL, INC., Menlo Park, CA (US)

( * ) Notice: Subject to any disclaimer, the term of this patent is extended or adjusted under 35 U.S.C. 154(b) by 0 days.

(21) Appl. No.: 18/510,295

(22) Filed: Nov. 15, 2023

(65) Prior Publication Data

US 2024/0084289 A1    Mar. 14, 2024

Related U.S. Application Data

(62) Division of application No. 16/146,901, filed on Sep. 28, 2018, now Pat. No. 11,851,650.

(60) Provisional application No. 62/564,891, filed on Sep. 28, 2017.

(51) Int. Cl.
| | |
|---|---|
| *C12N 15/10* | (2006.01) |
| *C12Q 1/6844* | (2018.01) |
| *C12Q 1/6869* | (2018.01) |
| *C12Q 1/6874* | (2018.01) |
| *C12Q 1/6886* | (2018.01) |

(Continued)

(52) U.S. Cl.
CPC ....... *C12N 15/1058* (2013.01); *C12N 15/101* (2013.01); *C12N 15/1093* (2013.01); *C12N 15/1096* (2013.01); *C12Q 1/6844* (2013.01); *C12Q 1/6869* (2013.01); *C12Q 1/6874* (2013.01); *C12Q 1/6886* (2013.01); *C40B 40/08* (2013.01); *C12Q 2600/106* (2013.01); *C12Q 2600/112* (2013.01); *C12Q 2600/118* (2013.01); *C12Q 2600/16* (2013.01); *C40B 20/00* (2013.01)

(58) Field of Classification Search
CPC .............. C12N 15/1058; C12N 15/101; C12N 15/1093; C12N 15/1096; C12Q 1/6844; C12Q 1/6869; C12Q 1/6874; C12Q 1/6886; C12Q 2600/106; C12Q 2600/112; C12Q 2600/118; C12Q 2600/16; C40B 40/08; C40B 20/00
USPC ......................................................... 435/6.14
See application file for complete search history.

(56) References Cited

U.S. PATENT DOCUMENTS

| | | |
|---|---|---|
| 4,683,195 A | 7/1987 | Mullis et al. |
| 6,818,395 B1 | 11/2004 | Quake et al. |
| 7,169,560 B2 | 1/2007 | Lapidus et al. |

(Continued)

FOREIGN PATENT DOCUMENTS

| | | | | |
|---|---|---|---|---|
| CN | 106867996 A | 6/2017 | | |
| WO | WO-2014008447 A1 * | 1/2014 | ......... | C12N 15/1003 |

(Continued)

OTHER PUBLICATIONS

Bettegowda, et al., "Detection of circulating tumor DNA in early- and late-stage human malignancies,", (2014) SciTrans Med 6(224):1-11.

(Continued)

*Primary Examiner* — Aaron A Priest
*Assistant Examiner* — Randi Lynn Beil
(74) *Attorney, Agent, or Firm* — Fenwick & West LLP

(57) ABSTRACT

Methods for preparing enriched sequencing libraries from test samples that contain double-stranded deoxyribonucleic acid (dsDNA) are provided.

17 Claims, 8 Drawing Sheets

(51) Int. Cl.
*C40B 20/00* (2006.01)
*C40B 40/08* (2006.01)

(56) References Cited

U.S. PATENT DOCUMENTS

| | | |
|---|---|---|
| 7,282,337 B1 | 10/2007 | Harris et al. |
| 7,666,593 B2 | 2/2010 | Lapidus |
| 2002/0164629 A1 | 11/2002 | Quake et al. |
| 2009/0026082 A1 | 1/2009 | Rothberg et al. |
| 2009/0127589 A1 | 5/2009 | Rothberg et al. |
| 2009/0156412 A1 | 6/2009 | Harris et al. |
| 2009/0191565 A1 | 7/2009 | Lapidus et al. |
| 2010/0035252 A1 | 2/2010 | Rothberg et al. |
| 2010/0137143 A1 | 6/2010 | Rothberg et al. |
| 2010/0167954 A1 | 7/2010 | Earnshaw et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2015/0087535 A1 | 3/2015 | Patel |
| 2015/0275290 A1 | 10/2015 | Osteras et al. |
| 2015/0353926 A1 | 12/2015 | Rigatti et al. |
| 2019/0085406 A1 | 3/2019 | Mortimer et al. |

FOREIGN PATENT DOCUMENTS

| | | |
|---|---|---|
| WO | 2014/043763 | 3/2014 |
| WO | 2016/008451 | 1/2016 |
| WO | 2017/012592 | 1/2017 |
| WO | 2018/085862 | 5/2018 |

OTHER PUBLICATIONS

Braslavsky et al., "Sequence information can be obtained from single DNA molecules," (2003) PNAS 100(7):3960-3964.

Duncavage et al., "Hybrid Capture and Next-Generation Sequencing Identify Viral Integration Sites from Formalin-Fixed, Paraffin-Embedded Tissue," (2011) J Mol Diagn. 13(3):325-333.

Harris et al., "Single-Molecule DNA Sequencing of a Viral Genome," (2008) Science 320:106-109.

Underhill et al., "Fragment Length of Circulating Tumor DNA," (2016) PLOS Genetics 12(7):e1006162.

Jiang et al., "Lengthening and Shortening of Plasma DNA in Hepatocellular Carcinoma Patients," (2015) Proceedings of the National Academy of Sciences of the United States of America, 112(11):E1317-E1325.

Marguiles et al., "Genome sequencing in microfabricated high-density picolitre reactors," (2005) Nature 437(7057):376-380.

Maxam et al., "A new method for sequencing DNA," (1977) PNAS 74(2):560-564.

Moudrianakis et al., "Base Sequence Determination in Nucleic Acids With the Electron Microscope III. Chemistry and microscopy of guanine-labeled DNA," (1965) PNAS 53(3):564-671.

Mouliere et al., "Circulating tumor-derived DNA is shorter than somatic DNA in plasma," (2015) PNAS 112(11):3178-3179.

Mouliere et al., "Multi-marker Analysis of Circulating Cell-free DNA Toward Personalized Medicine for Colorectal Cancer," (2014) Mol Oncol. 8(5):927-947.

Newman et al., "An ultrasensitive method for quantitating circulating tumor DNA with broad patient coverage," (2014) Nat Med 20(5):548-554.

Sanger et al., "DNA sequencing with chain-terminating inhibitors," (1977) PNAS 74(12):5463-5467.

Soni et al., "Progress toward ultrafast DNA sequencing using solid-state nanopores," (2007) Clin. Chem, 53(11):1996-2001.

Yu et al., "Size-based Molecular Diagnostics Using Plasma DNA for Noninvasive Prenatal Testing," (2014) Proceedings of the National Academy of Sciences of the United States of America, 111(23): 8583-8588.

Shendure et al., "Next-generation DNA Sequencing," (2009) Nature 26(10):1135-1145.

Yang et al., "Size-selective separation and overall-amplification of cell-free DNA fragments using PCR-based enrichment," (2017) Scientific Reports 7(1):40936.

Moulier et al., "High Fragmentation Characterizes Tumor-derived Circulating DNA," (2011) PLoS ONE 6(9):e23418.

* cited by examiner

ENRICHMENT OF SHORT NUCLEIC ACID FRAGMENTS IN SEQUENCING LIBRARY PREPARATION

CROSS-REFERENCE TO RELATED APPLICATIONS

This application is a divisional of U.S. application Ser. No. 16/146,901, filed Sep. 28, 2018, and entitled "Enrichment Of Short Nucleic Acid Fragments In Sequencing Library Preparation," the disclosure of which is incorporated by reference herein in its entirety. Under 35 U.S.C. § 119(e), U.S. application Ser. No. 16/146,901 claims priority benefit of the filing date of U.S. Provisional Patent Application No. 62/564,891, filed on Sep. 28, 2017, the disclosure of which application is herein incorporated by reference in its entirety.

FIELD OF THE INVENTION

The present invention relates to methods for preparing enriched sequencing libraries from test samples that contain double-stranded deoxyribonucleic acid (dsDNA).

BACKGROUND OF THE INVENTION

Analysis of circulating cell-free nucleic acids (e.g., cell-free DNA (cfDNA)) using next generation sequencing (NGS) is recognized as a valuable diagnostic tool for many diseases. Using current library preparation protocols for preparing cfDNA for sequencing tends to result in sequencing libraries where a majority of the recovered nucleic acid fragments are greater than 150 bp in length. However, recent research suggests that cfDNA fragmentation patterns (which can be determined though fragment size analysis, methylation profiling, endpoints positions, nucleosome protection regions, transcription factor protected regions, etc.) may provide rich information to detect cancer, classify cancer, monitor cancer progression, or for determining tissue of origin for detected cfDNA fragments. Moreover, the signal from shorter nucleic acid fragments may be buried in non-informative reads obtained from relatively longer nucleic acid fragments. That is, most of sequencing reads may not be informative. Accordingly, there is a need in the art for new methods for preparing sequencing libraries from cell-free DNA containing test samples that are enriched for shorter nucleic acid fragments (e.g., less than 150 bp in length).

SUMMARY OF THE INVENTION

The present invention is directed to methods for preparing an enriched sequencing library from a double-stranded deoxyribonucleic acid (dsDNA) containing test sample. In one aspect, the present invention is directed to methods for preparing a sequence library that is enriched for shorter nucleic acid fragments (e.g., nucleic acid fragments less than about 150 bp in length). In some embodiments, the library can be used for detecting cancer, screening for cancer, determining cancer stage or status, monitoring cancer progression and/or classifying cancer (e.g., cancer type and/or tissue of origin). In some embodiments, a sequencing library prepared with biased size selection, to enrich for shorter nucleic acid, is used to enrich for informative nucleic acid fragments and/or reduce sequencing burden.

In one embodiment, the present invention is directed to a method for preparing an enriched sequencing library, the method comprising: (a) obtaining a test sample comprising a plurality of double-stranded deoxyribonucleic acid (dsDNA) fragments; (b) enriching the sample for dsDNA fragments below a size threshold to generate an enriched sample, wherein the size threshold is less than about 150 bp in length; and (d) preparing a sequencing library from the enriched sample. In one embodiment, the sequencing library is considered to be enriched for dsDNA fragments less than about 150 bp in length when the proportion of dsDNA fragments less than about 150 bp in length is higher compared to a sequencing library prepared from a test sample without a size based enrichment step. In another embodiment, after enrichment, dsDNA fragments below a size threshold (e.g., less than about 150 bp, less than about 140 bp, less than about 120 bp, or less than about 100 bp in length) comprises more than 25%, more than 30%, more than 40%, or more than 50% of the dsDNA molecules in the test sample.

In another embodiment, the present invention is directed to a method for preparing an enriched sequencing library, the method comprising: (a) obtaining a test sample comprising a plurality of double-stranded deoxyribonucleic acid (dsDNA) fragments; (b) ligating double-strand DNA (dsDNA) adapters to both ends of the dsDNA fragments to generate a plurality of adapter-fragment constructs, wherein the dsDNA adapter comprises a first strand and a second strand; (c) amplifying the adapter-fragment constructs to generate a sequencing library, wherein the adapter-fragment constructs are amplified in the presence of a blocker, the blocker comprising an oligonucleotide sequence having sequence complementarity with at least a portion of the 5'-end of the first strand and at least a portion of the 3'-end of the second strand; wherein the sequencing library is enriched for adapter-fragment constructs derived from dsDNA fragments below a size threshold to generate an enriched sample, wherein the size threshold is less than about 150 bp in length. In one embodiment, the sequencing library is considered to be enriched for adapter-fragment constructs derived from fragments less than about 150 bp in length when the proportion of adapter-fragment constructs derived from fragments less than 150 bp in length is higher compared to a sequencing library prepared without a size based enrichment step. In another embodiment, after enrichment, adapter-fragment constructs derived from dsDNA fragments below a size threshold (e.g., less than about 150 bp, less than about 140 bp, less than about 120 bp, or less than about 100 bp in length) comprises more than 25%, more than 30%, more than 40%, or more than 50% of the dsDNA molecules in the test sample.

In still another embodiment, the present invention is directed to a method for preparing an enriched sequencing library, the method comprising: (a) obtaining a test sample comprising a plurality of double-stranded deoxyribonucleic acid (dsDNA) fragments; (b) preparing an enriched sequencing library from the test sample, wherein preparing the sequencing library comprises: (i) ligating double-strand DNA adapters to both ends of the dsDNA fragments to generate a plurality of adapter-fragment constructs; (ii) adding a first set of primers to the adapter-fragment constructs, wherein the first set of primers comprise single-stranded oligonucleotide less than about 50 nucleotides in length; (iii) hybridizing the first set of primers to the adapter-fragment constructs and extending the first set of primers in a first nucleic acid extension reaction using a polymerase to generate a plurality of amplified adapter-fragment constructs; (iii) enriching the amplified adapter-fragment constructs for adapter-fragment constructs derived from dsDNA fragments below a size threshold to generate an enriched sample, wherein the size threshold is less than about 150 bp in length; (iv) adding a second set of primers to the enriched sample, wherein the second set of primers comprise single-stranded oligonucleotide greater than about 50 nucleotides in length; and (v) hybridizing the second set of primers to the enriched adapter-fragment constructs and extending the second set of primers in a second nucleic acid extension reaction using a polymerase to generate a sequencing library. In one embodiment, the sequencing library is considered to be enriched for adapter-fragment constructs derived from fragments less than about 150 bp in length when the proportion of adapter-fragments derived from fragments less than about 150 bp in length is higher compared to a sequencing library prepared without a size based enrichment step. In another embodiment, after enrichment, adapter-fragment constructs derived from dsDNA fragments below the size threshold (e.g., less than about 150 bp, less than about 140 bp, less than about 120 bp, or less than about 100 bp in length) comprises more than 25%, more than 30%, more than 40%, or more than 50% of the dsDNA molecules in the test sample.

In yet another embodiment, the present invention is directed to a method for preparing an enriched sequencing library, the method comprising: (a) obtaining a test sample comprising a plurality of double-stranded deoxyribonucleic acid (dsDNA) fragments; (b) ligating double-strand DNA (dsDNA) adapters to both ends of the dsDNA fragments to generate a plurality of adapter-fragment constructs, wherein the dsDNA adapters are shorter than 50 bp in length; (c) amplifying the plurality of adapter-fragment constructs to generate a sequencing library; (d) incubate the sequencing library at from about 55° C. to about 75° C. for from about 5 min. to about 20 min, wherein said incubation step denatures adapter dimers, and wherein adapter-fragment constructs are not denatured; and (e) enriching the sequencing library for adapter-fragment constructs derived from dsDNA fragments less than about 150 bp in length to generate an enriched sequencing library. In one embodiment, the sequencing library is enriched for adapter-fragment constructs derived from fragments less than about 150 bp in length compared to a sequencing library prepared from a test sample that has not been enriched. In another embodiment, after enrichment, adapter-fragment constructs derived from dsDNA fragments below the size threshold (e.g., less than about 150 bp, less than about 140 bp, less than about 120 bp, or less than about 100 bp in length) comprises more than 25%, more than 30%, more than 40%, or more than 50% of the dsDNA molecules in the test sample.

In one aspect of the present invention the test sample may comprise a plurality of dsDNA fragments synthesized from single-stranded ribonucleic acid (ssRNA) molecules, wherein synthesizing the dsDNA fragments from ssRNA molecules comprises: (a) obtaining a test sample comprising a plurality of single-stranded ribonucleic acid (ssRNA) molecules; (b) adding an RNA primer to the ssRNA test sample and extending the RNA primer in a first nucleic acid extension reaction using reverse transcriptase to generate a plurality of complementary DNA (cDNA) sequences, wherein the cDNA sequences are complementary to the one or more RNA templates; and (c) adding one or more DNA primers to the reaction mixture and extending the one or more DNA primers in a second nucleic acid extension reaction using a DNA polymerase to generate a plurality of dsDNA fragments.

In accordance with other aspects, the sequencing library prepared using the methods of the present invention can be sequenced to obtain a plurality of sequence reads, and the sequence reads analyzed to detect the presence or absence of cancer, screen for cancer, determine cancer stage or status, monitor cancer progression, and/or determine a cancer classification. In other embodiments, the sequence reads can be analyzed to determine cancer type and/or cancer tissue of origin. In still other embodiments, the sequence reads can be analyzed to monitor disease progression, monitor therapy, and/or monitor cancer growth. In accordance with these embodiments, the cancer may comprise a carcinoma, a sarcoma, a myeloma, a leukemia, a lymphoma, a blastoma, a germ cell tumor, or any combination thereof.

In another aspect, the present invention is directed to methods for preparing an enriched sequencing library from a test sample comprising a plurality of cell-free nucleic acids (e.g., cfDNA and/or cfRNA) fragments.

DEFINITIONS

Figure 1:
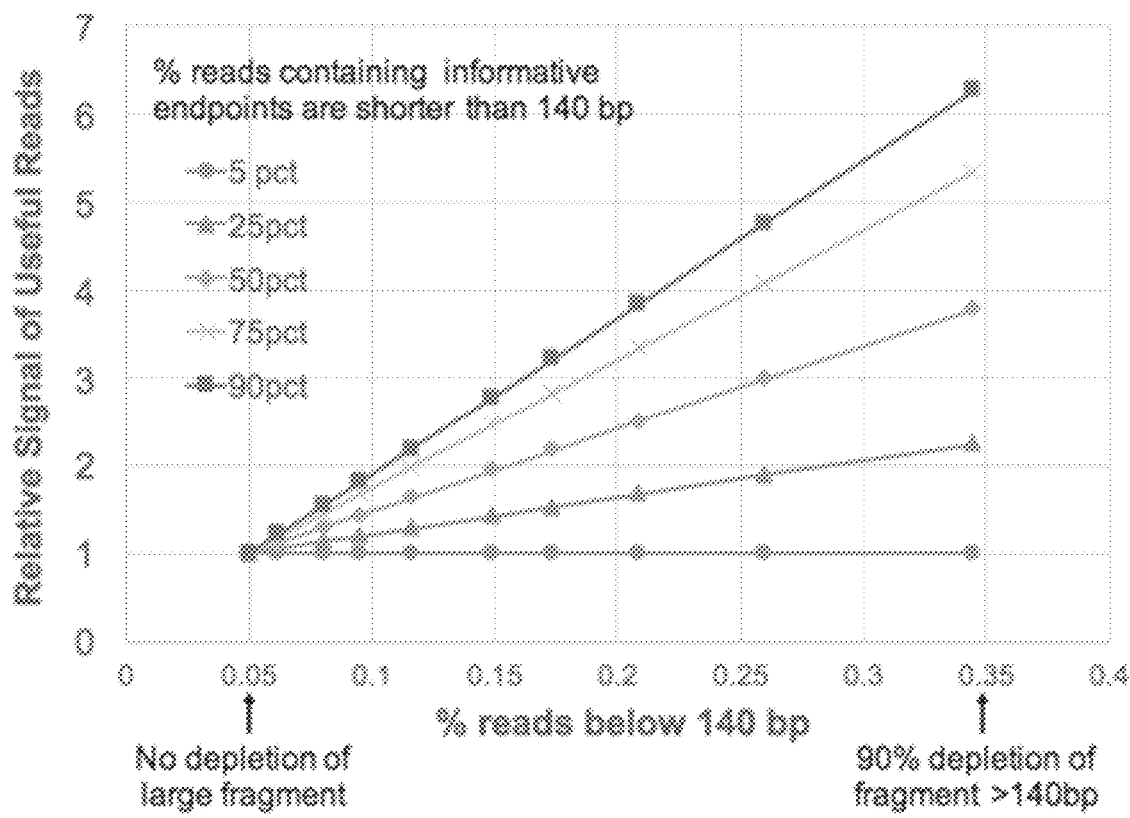
FIG. 1 is a schematic showing the percentage of sequence reads below 140 bp in test samples with 5%, 25%, 50%, 75% and 90% depletion of fragments greater than 140 bp.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, NY 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al., Cellular and Molecular Immunology, 6th edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al., U.S. Pat. Nos. 4,683,195; 4,965,188; 4,683,202; 4,800,159 (PCR); Gelfand et al., U.S. Pat. No. 5,210,015 (real-time PCR with "taqman" probes); Wittwer et al., U.S. Pat. No. 6,174,670; Kacian et al., U.S. Pat. No. 5,399,491 ("NASBA"); Lizardi, U.S. Pat. No. 5,854,033; Aono et al., Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al., Nucleic Acids Research, 26: 2150-2155 (1998), and like references.

The term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N. Y. (2001) ("Sambrook et al.) which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred L, e.g., 200 µL. "Reverse transcription PCR," or "RT-PCR," means a PCR that is preceded by a reverse transcription reaction that converts a target RNA to a complementary single stranded DNA, which is then amplified, an example of which is described in Tecott et al., U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("taqman"); Wittwer et al., U.S. Pat. Nos. 6,174,670 and 6,569,627 (intercalating dyes); Tyagi et al., U.S. Pat. No. 5,925,517 (molecular beacons); the disclosures of which are hereby incorporated by reference herein in their entireties. Detection chemistries for real-time PCR are reviewed in Mackay et al., Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al., Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references, which are incorporated by reference herein in their entireties: Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); and Becker-Andre et al., Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, 2nd Edition (Cold Spring Harbor Press, New York, 2003).

The terms "subject" and "patient" are used interchangeably herein and refer to a human or non-human animal who is known to have, or potentially has, a medical condition or disorder, such as, e.g., a cancer.

The term "sequence read" as used herein refers to nucleotide sequences read from a sample obtained from a subject. Sequence reads can be obtained through various methods known in the art.

The term "read segment" or "read" as used herein refers to any nucleotide sequences, including sequence reads obtained from a subject and/or nucleotide sequences, derived from an initial sequence read from a sample. For example, a read segment can refer to an aligned sequence read, a collapsed sequence read, or a stitched read. Furthermore, a read segment can refer to an individual nucleotide base, such as a single nucleotide variant.

The term "enrich" as used herein means to increase a proportion of one or more nucleic acids based on size (or nucleic acid length) in a sample or sequencing library. An "enriched" sample or sequencing library is therefore a sample or sequencing library in which a proportion of nucleic acids below a size threshold (e.g., less than 150 bp, less than 140 bp, less than 120 bp, or less than 100 bp in length), has been increased with respect to the total nucleic acid content in the sample. For example, a sample or sequencing library can be enriched using one of the methods disclosed herein compared to a sample or sequencing library prepared from a test sample without a size-based enrichment step. In one embodiment, dsDNA molecules or fragments below a size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample. In another embodiment, adapter-fragment constructs derived from dsDNA fragments below the size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample.

The term "cell-free nucleic acid" or "cfNA" refers to nucleic acid fragments (DNA, RNA) that circulate in a subject's body (e.g., bloodstream) and originate from one or more healthy cells and/or from one or more cancer cells.

The term "circulating tumor nucleic acid" or "ctNA" refers to nucleic acid fragments (DNA, RNA) that originate from tumor cells or other types of cancer cells, which may be released into a subject's bloodstream as a result of biological processes, such as apoptosis or necrosis of dying cells, or may be actively released by viable tumor cells.

DETAILED DESCRIPTION OF THE INVENTION

The present invention is generally directed to methods for preparing an enriched sequencing library. In certain aspects, the present methods can be used to enrich a sequencing library for dsDNA fragments below a given size threshold (e.g., <150 bp, <140 bp, or <100 bp). In some embodiments of the present invention, a sequencing library prepared with biased size selection, to enrich for shorter nucleic acid fragments, is used to enrich for informative nucleic acid fragments and/or reduce sequencing burden.

Typical cfDNA has tight size distribution with mononucleosome peak of approximately 167 bp. Using a conventional library preparation process, only approximately 5% of fragments obtained from a blood sample are shorter than 140 bp in length (See FIG. 1). As shown in FIG. 1, Applicants have discovered that library preparation with biased size selection can enrich shorter nucleic acid fragments or nucleic acids below a given size ratio (e.g., fragments less than 140 bp in length), which can provide informative fragments for analysis and/or reduce sequencing requirements in disease assessment from cell-free nucleic acid samples. For example, as shown in FIG. 1, if 90% of informative nucleic acid fragments are shorter than 140 bp in length, than the sequencing signal can be enhanced by more than 6-fold by depleting 90% of fragments longer than 140 bp. Moreover, where short nucleic acids are informative (fragments less than 140 bp in length), enriching a sequencing library for nucleic acid fragments under 140 bp in length allows for the same sensitivity to be achieved with 6-fold less sequencing throughput.

The present invention describes various methods for preparing an enriched sequencing library from a test sample. For example, a size selection step can be performed to enrich a sequencing library for fragments above, or under a selected size. The size selection step can be before the library preparation (i.e., cfDNA input size selection), during the library preparation, or after library preparation. In some embodiment, the enriched sequencing library can be used for detecting cancer, screening for cancer, determining cancer stage or status, monitoring cancer progression, and/or determining a cancer classification.

Figure 2:
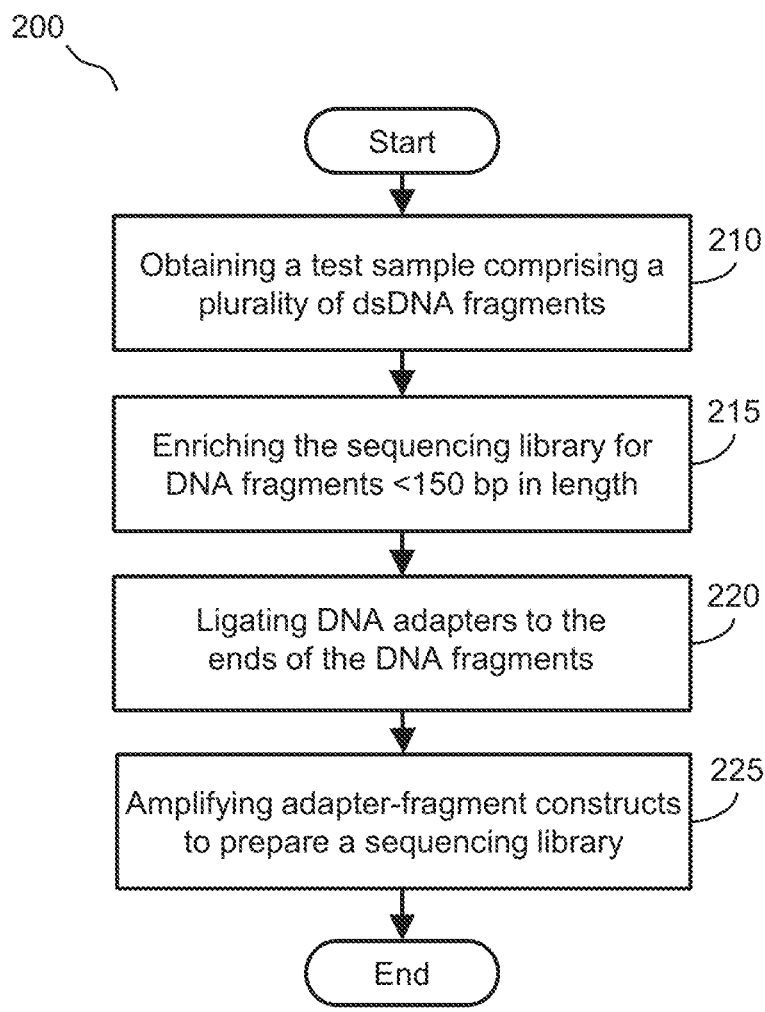
FIG. 2 is a flow diagram illustrating a method for preparing an enriched sequencing library, in accordance with one embodiment of the present invention.

FIG. 2 is a flow diagram illustrating a method 200 for preparing an enriched sequencing library from a test sample comprising a plurality of double-stranded DNA (dsDNA) fragments, in accordance with one embodiment of the present invention. As shown in FIG. 2, at step 210, a test sample (e.g., a biological test sample) is obtained from a subject (e.g., a patient). In one embodiment, the test sample may be a biological test sample selected from the group consisting of blood, plasma, serum, urine, saliva, fecal samples, and any combination thereof. Alternatively, the test sample or biological test sample may comprise a test sample selected from the group consisting of whole blood, a blood fraction, a tissue biopsy, pleural fluid, pericardial fluid, cerebral spinal fluid, and peritoneal fluid. In other embodiments, the sample is a plasma sample from a cancer patient, or a patient suspected of having cancer. In accordance with some embodiments, the test sample or biological test sample comprises a plurality of cell-free nucleic acids (e.g., cell-free DNA (cfDNA) and/or cell-free RNA (cfRNA)) fragments. In other embodiments, the test sample or biological test sample comprises a plurality of cell-free nucleic acids (e.g., cell-free DNA and RNA) fragments originating from healthy cells and from cancer cells. In some embodiments, the test sample comprises a plurality of circulating tumor DNA (ctDNA). Optionally, in one embodiment, cell-free nucleic acids (e.g., cfDNA and/or cfRNA) can be extracted and/or purified from the test sample before proceeding with subsequent library preparation steps. In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (Qiagen, Germantown, MD) or MagMAX Cell-Free DNA Isolation Kit (Thermo Fisher Scientific, Waltham, MA).

In accordance with the present invention, as shown in step 215, the test sample may be enriched for shorter dsDNA fragments, or dsDNA fragments below a size threshold, using a size selection step. In one embodiment, dsDNA fragments less than about 150 bp in length are enriched for in the sample. In other embodiments, dsDNA fragments less than about 140 bp, less than about 130 bp, less than about 120 bp, less than about 110 bp, less than about 100 bp, less than about 90 bp, less than about 80 bp, less than about 70 bp, or less than about 60 bp in length are enriched. In another embodiment, dsDNA fragments from about 40 bp to about 150 bp in length, from about 60 bp to about 140 bp, from about 70 bp to about 130 bp, or from about 80 bp to about 120 bp in length are enriched. In general, any known means in the art can be used to enrich dsDNA fragments. For example, the size selection can be achieved using size selection beads, for example, solid phase reversible immobilization (SPRI) beads (AMPure XP size selection beads, New England BioLabs, Ipswich, MA), or a gel-electrophoresis based method. In another embodiment, a post library preparation clean-up step, e.g., using a PCR cleanup or bead based clean up (e.g., SPRI beads) can also be utilized to remove adapter-fragment constructs derived from dsDNA fragments above a desired cut off length (e.g., derived from dsDNA fragments>150 bp). In one embodiment, the sequencing library is considered to be enriched for dsDNA fragments less than about 150 bp in length when the proportion of dsDNA fragments less than about 150 bp in length is higher compared to a sequencing library prepared from a test sample without a size based enrichment step. In another embodiment, after enrichment, dsDNA fragments below a size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample.

At step 220 double-strand DNA adapters are ligated to the ends of the dsDNA molecules obtained from step 210 to generate a plurality of dsDNA adapter-fragment constructs. The ligation reaction can be performed using any suitable ligation step (e.g., using a ligase) which joins the dsDNA adapters to the dsDNA fragments to form dsDNA adapter-fragment constructs. In one example, the ligation reaction is performed using T4 DNA ligase. In another example, T7 DNA ligase is used for adapter ligation to the modified nucleic acid molecule.

In one embodiment, the ends of dsDNA molecules are repaired using, for example, T4 DNA polymerase and/or Klenow polymerase and phosphorylated with a polynucleotide kinase enzyme prior to ligation of the adapters. A single "A" deoxynucleotide is then added to the 3' ends of dsDNA molecules using, for example, Taq polymerase enzyme, producing a single base 3' overhang that is complementary to a 3' base (e.g., a T) overhang on the dsDNA adapter.

In one embodiment, the sequencing adapters can include a unique molecular identifier (UMI) sequence, such that, after library preparation, the sequencing library will include UMI tagged amplicons derived from dsDNA fragments. In one embodiment, unique sequence tags (e.g., unique molecular identifiers (UMIs)) can be used to identify unique nucleic acid sequences from a test sample. For example, differing unique sequence tags (UMIs) can be used to differentiate various unique nucleic acid sequence fragments originating from the test sample. In another embodiment, unique sequence tags (UMIs) can be used to reduce amplification bias, which is the asymmetric amplification of different targets due to differences in nucleic acid composition (e.g., high GC content). The unique sequence tags (UMIs) can also be used to discriminate between nucleic acid mutations that arise during amplification. In one embodiment, the unique sequence tag can comprise a short oligonucleotide sequence having a length of from about 2 nt to about 100 nt, from about 2 nt to about 60 nt, from about 2 to about 40 nt, or from about 2 to about 20 nt. In another embodiment, the UMI tag may comprise a short oligonucleotide sequence greater than about 5, 6, 7, 8, 9, 10, 11, 12, 13, 14, 15, 16, 17, or 18 nucleotides (nt) in length.

The unique sequence tags can be present in a multi-functional nucleic acid sequencing adapter, which sequencing adapter can comprise a unique sequence tag and/or a universal priming site. In another embodiment, the sequencing adapters utilized may include a universal primer and/or one or more sequencing oligonucleotides for use in subsequent cluster generation and/or sequencing (e.g., known P5 and P7 sequences for used in sequencing by synthesis (SBS) (Illumina, San Diego, CA)).

At step 225 the dsDNA adapter-fragment constructs are amplified to generate a sequencing library. For example, the adapter-modified dsDNA molecules can be amplified by PCR using a DNA polymerase and a reaction mixture containing primers.

After library preparation, the sequencing library can be sequenced to obtain sequence data or sequence reads and the sequence data or reads analyzed. In one embodiment, the sequence data or reads can be analyzed for use in detecting cancer, screening for cancer, determining cancer stage or status, monitoring cancer progression and/or classifying cancer (not shown)

Figure 3:
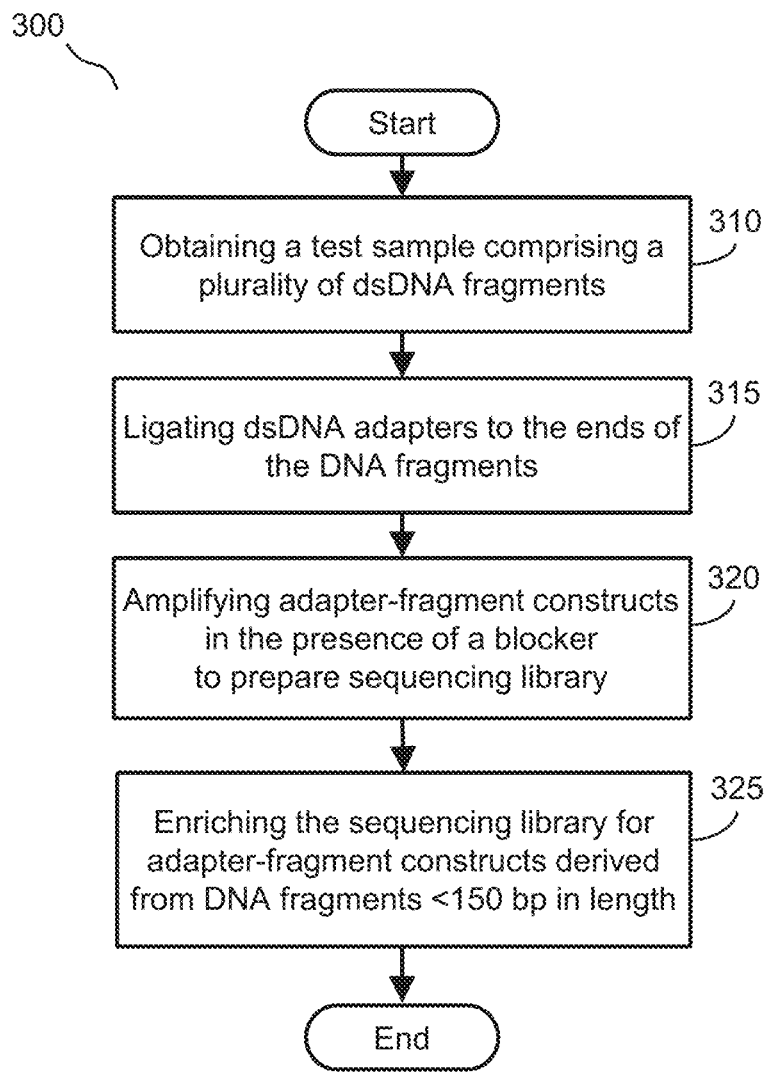
FIG. 3 is a flow diagram illustrating a method for preparing an enriched sequencing library using a blocker, in accordance with another embodiment of the present invention.

FIG. 3 is a flow diagram illustrating a method 300 for preparing an enriched sequencing library from a test sample comprising a plurality of double-stranded DNA (dsDNA) fragments, in accordance with another embodiment of the present invention. As shown in FIG. 3, at step 310, a test sample (e.g., a biological test sample) is obtained from a subject (e.g., a patient). As noted above, the test sample or biological test sample may be a sample selected from the group consisting of blood, whole blood, a blood fraction, plasma, serum, urine, saliva, a tissue biopsy, pleural fluid, pericardial fluid, cerebral spinal fluid, peritoneal fluid sample, and any combination thereof. The test sample or biological test sample may comprise a plurality of cell-free nucleic acids (e.g., cell-free DNA (cfDNA) and/or cell-free RNA (cfRNA)) fragments. In some aspects, the test sample or biological test sample comprises a plurality of cell-free nucleic acids (e.g., cell-free DNA and RNA) fragments originating from healthy cells and from cancer cells. In some embodiments, the test sample comprises a plurality of circulating tumor DNA (ctDNA). Optionally, in one embodiment, cell-free nucleic acids (e.g., cfDNA and/or cfRNA) can be extracted and/or purified from the test sample or biological test sample before proceeding with subsequent library preparation steps. In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (Qiagen, Germantown, MD) of MagMAX Cell-Free DNA Isolation Kit (Thermo Fisher Scientific, Waltham, MA).

At step 315 double-strand DNA adapters are ligated to the dsDNA molecules obtained from step 310 in a ligation reaction to generate a plurality of dsDNA adapter-fragment constructs. The ligation reaction can be performed using any suitable ligation step (e.g., using a ligase) which joins the dsDNA adapters to the dsDNA fragments to form dsDNA adapter-fragment constructs. In one example, the ligation reaction is performed using T4 DNA ligase. In another example, T7 DNA ligase is used for adapter ligation to the modified nucleic acid molecule. As described above, the ends of the dsDNA molecules may be repaired, phosphorylated and/or end-tailed prior to ligation of adapters to the ends of the dsDNA molecules.

As noted above, the dsDNA adapters may comprise a unique molecular identifier (UMI) sequence. The unique sequence tag can comprise a short oligonucleotide sequence having a length of from about 2 nt to about 100 nt, from about 2 nt to about 60 nt, from about 2 to about 40 nt, or from about 2 to about 20 nt. In another embodiment, the UMI tag may comprise a short oligonucleotide sequence greater than about 5, 6, 7, 8, 9, 10, 11, 12, 13, 14, 15, 16, 17, or 18 nucleotides (nt) in length. Also like the ssDNA adapters described above, the dsDNA adapters may include a universal primer and/or one or more sequencing oligonucleotides for use in subsequent cluster generation and/or sequencing (e.g., known P5 and P7 sequences for used in sequencing by synthesis (SBS) (Illumina, San Diego, CA)).

At step 320 the dsDNA adapter-fragment constructs are amplified to generate a sequencing library. In accordance with one embodiment, the adapter-fragment constructs are amplified in the presence of a blocker used to reduce amplification of adapter dimers. For example, the adapter-constructs may be amplified by PCR using a DNA polymerase and a reaction mixture containing primers, a plurality of dNTPs and a blocker. In one embodiment, the blocker comprises a 5' to 3' oligonucleotide sequence having sequence complementarity with at least a portion of the 5'-end of the first strand and at least a portion of the 3'-end of the second strand. The ssDNA oligonucleotide blocker may include a blocking nucleotide, such as a dideoxynucleotide base, at the 3'-end of the blocker prohibiting extension of the blocker during an extension reaction. In another embodiment, the blocker may comprise one or more modified bases (e.g., a locked nucleic acid (LNA) base) having a higher melting temperature than standard DNA bases. The use of modified bases having higher melting temperatures to increase, or strengthen, hybridization of the blocker to the adapter dimer.

Figure 4:
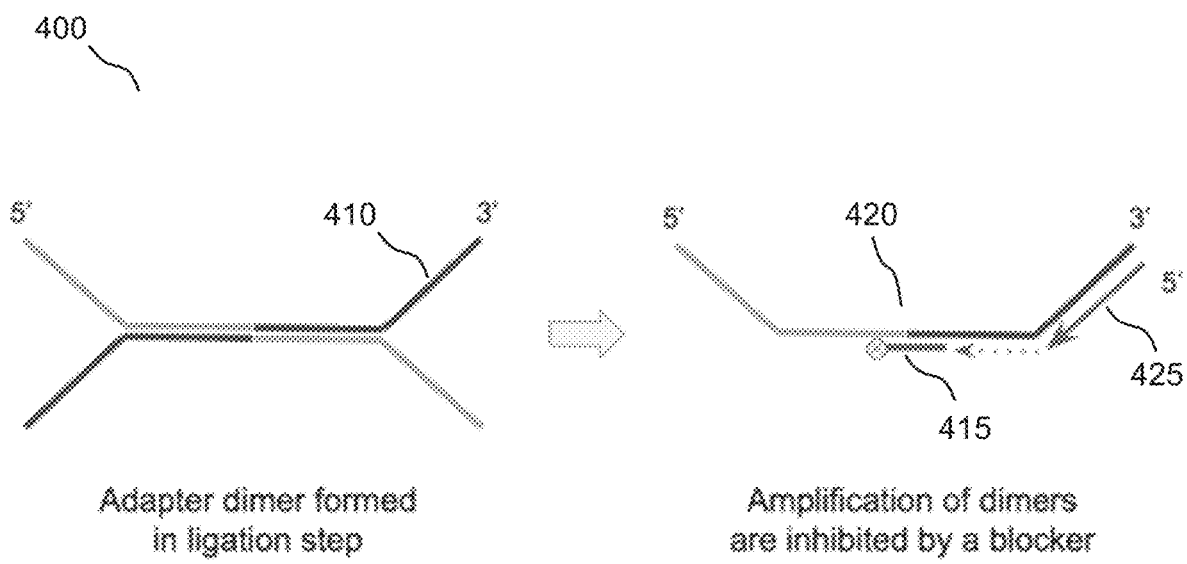
FIG. 4 shows pictorially amplification inhibition of an adapter in the presence of a blocker, in accordance with the embodiment illustrated in FIG. 3.

As is well known in the art and illustrated in FIG. 4, during library preparation, the double-strand DNA adapters 410 used in step 315 can ligate together to form an adapter dimer 400. Also, as shown in FIG. 4, the ssDNA oligonucleotide blocker 415 used in the practice of this embodiment may be designed to hybridize across the junction 420 of the adapter dimer 400 inhibiting amplification of the adapter dimers. By designing the ssDNA oligonucleotide blocker to hybridize across the junction of the adapter dimer, amplification of the adapter dimer can be inhibited during amplification 425 of the library without inhibition of adapter-fragment constructs.

As shown in step 325, the sequencing library from step 320 is enriched for adapter-fragment constructs derived from nucleic acids (e.g., dsDNA fragments) below a size threshold (e.g., less than about 150 bp, less than about 140 bp, less than about 120 bp, or less than about 100 bp in length), using a size selection step. The use of an oligonucleotide blocker 415 prevents amplification of adapter dimers, which would otherwise be difficult to separate from adapter-fragment constructs derived from nucleic acids below the size threshold due to overall size (or length) similarities, and thus allows for more efficient size based enrichment of adapter-fragment constructs derived from dsDNA fragments below the size threshold (as described below, e.g., in conjunction with FIG. 6A-B). For example, in one embodiment, a size selection step is used to enrich for fragments from the original sample that are shorter than 150 bp in length (i.e., fragments less than 150 bp in length not including the length of the adapters used) to generate an enriched sample. In one embodiment, dsDNA fragments (minus the adapters) less than about 150 bp, less than about 140 bp, less than about 130 bp, less than about 120 bp, less than about 110 bp, less than about 100 bp, less than about 90 bp, less than about 80 bp, less than about 70 bp, or less than about 60 bp in length are enriched. In another embodiment, dsDNA fragments from about 40 bp to about 150 bp in length (minus the adapters), from about 60 bp to about 140 bp, from about 70 bp to about 130 bp, or from about 80 bp to about 120 bp, are enriched.

In general, any known means in the art can be used to enrich dsDNA fragments. For example, size selection can be performed before the library preparation (i.e., cfDNA input size selection) or during the library preparation. In general, any known means in the art can be used to enrich dsDNA fragments. For example, the size selection can be achieved using size selection beads, for example, solid phase reversible immobilization (SPRI) beads (AMPure XP size selection beads, New England BioLabs, Ipswich, MA), or a gel-electrophoresis based method. In another embodiment, a post library preparation clean-up step, e.g., using a PCR cleanup or bead based clean up (e.g., SPRI beads) can also be utilized to remove adapter-fragment constructs derived from dsDNA fragments above a desired cut off length (e.g., derived from dsDNA fragments>150 bp). In one embodiment, the sequencing library is considered to be enriched for adapter-fragment constructs derived from fragments less than about 150 bp in length when the proportion of adapter-fragment constructs derived from fragments less than 150 bp in length is higher compared to a sequencing library prepared without a size based enrichment step. In another embodiment, after enrichment, adapter-fragment constructs derived from dsDNA fragments below a size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample.

After enrichment, the enriched sequencing library can be sequenced to obtain sequence data or sequence reads and the sequence data or reads analyzed. In one embodiment, the sequence data or reads can be analyzed for use in detecting cancer, screening for cancer, determining cancer stage or status, monitoring cancer progression and/or classifying cancer (not shown).

Figure 5:
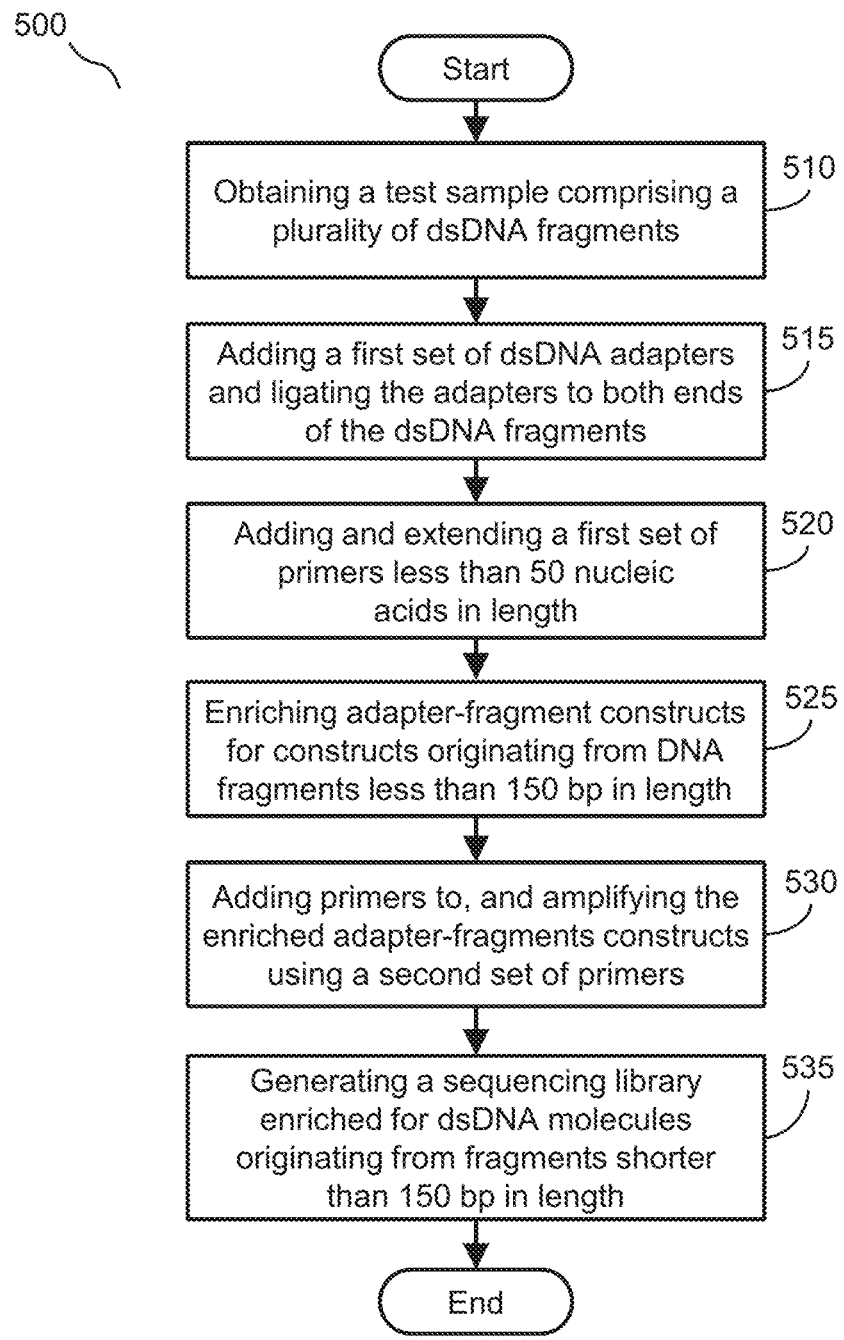
FIG. 5 is a flow diagram illustrating a method for preparing an enriched sequencing library using a two-step amplification process, in accordance with another embodiment of the present invention.

FIG. 5 is a flow diagram illustrating a method 500 for preparing an enriched sequencing library from a test sample comprising a plurality of double-stranded DNA (dsDNA) fragments, in accordance with one embodiment of the present invention. As shown in FIG. 5, at step 510, a test sample (e.g., a biological test sample) is obtained from a subject (e.g., a patient). As noted above, the test sample may be a biological test sample selected from the group consisting of blood, whole blood, a blood fraction, plasma, serum, urine, fecal, saliva, a tissue biopsy, pleural fluid, pericardial fluid, cerebral spinal fluid, peritoneal fluid sample, and any combination thereof. In certain aspects, the test sample or biological test sample comprises a plurality of cell-free nucleic acids (e.g., cell-free DNA (cfDNA) and/or cell-free RNA (cfRNA)) fragments. In some embodiments, the test sample comprises a plurality of circulating tumor DNA (ctDNA). In certain embodiments, the test sample or biological test sample comprises a plurality of cell-free nucleic acids (e.g., cell-free DNA and RNA) fragments originating from healthy cells and from cancer cells. In one embodiment, cell-free nucleic acids (e.g., cfDNA and/or cfRNA) can be extracted and/or purified from the test sample (using a commercially available kit, as noted above) before proceeding with subsequent library preparation steps.

At step 515 double-strand DNA adapters are ligated to the dsDNA molecules obtained from step 510 in a ligation reaction to generate a plurality of dsDNA adapter-fragment constructs. The ligation reaction can be performed using any suitable ligation step (e.g., using a ligase) which joins the dsDNA adapters to the dsDNA fragments to form dsDNA adapter-fragment constructs. In one example, the ligation reaction is performed using T4 DNA ligase. In another example, T7 DNA ligase is used for adapter ligation to the modified nucleic acid molecule. As described above, the ends of the dsDNA molecules may be repaired, phosphorylated and/or end-tailed prior to ligation of adapters to the ends of the dsDNA molecules.

As noted above, the dsDNA adapters may comprise a unique molecular identifier (UMI) sequence. The unique sequence tag can comprise a short oligonucleotide sequence having a length of from about 2 nt to about 100 nt, from about 2 nt to about 60 nt, from about 2 to about 40 nt, or from about 2 to about 20 nt. In another embodiment, the UMI tag may comprise a short oligonucleotide sequence greater than about 5, 6, 7, 8, 9, 10, 11, 12, 13, 14, 15, 16, 17, or 18 nucleotides (nt) in length. Also like the ssDNA adapters described above, the dsDNA adapters may include a universal primer and/or one or more sequencing oligonucleotides for use in subsequent cluster generation and/or sequencing (e.g., known P5 and P7 sequences for used in sequencing by synthesis (SBS) (Illumina, San Diego, CA)).

As shown in FIG. 5, step 520, the adapter-fragment constructs can be amplified using a first extension reaction to generate a sample comprising a plurality of amplified adapter-fragment constructs. In some embodiments, a first set of primers comprising single-stranded DNA (ssDNA) oligonucleotides having a length of less than 50 bp are used in the extension reaction. In some embodiments, the set of primers comprise ssDNA oligonucleotides having a length less than 40 bp, less than 30 bp, or less than 20 bp. In another embodiment, the first set of primers comprise ssDNA oligonucleotides having a length of less than 50 bp and a 3'-end portion that is complementary to, and thus, hybridizes to the adapters used in step 315. The complementary 3'-end may comprise at least about 10 bp, at least about 20 bp, at least about 30, or at least about 40 bp, of the 3'-end of the first set of adapters. In another embodiment, the complementary 3'-end may comprise from about 10 to about 40 bp, from about 15 bp to about 25 bp, or from about 20 bp to about 40 bp, of the 3'-end of the first set of adapters. In still another embodiment, as shown for example in FIG. 6B, the first set of primers comprises a 30 bp ssDNA oligonucleotide having a 20 bp complementary 3'-end that hybridizes the adapter. The first set of primers can be used in an extension reaction (e.g., using polymerase chain reaction (PCR)) to amplify the adapter-fragment constructs generated in step 515.

In accordance with the present invention, as shown in step 525, the sample from step 520 is enriched for adapter-fragment constructs derived from nucleic acids (dsDNA fragments) below a size threshold (e.g., less than about 150 bp, less than about 140 bp, less than about 120 bp, or less than about 100 bp in length) using a size selection step. For example, in one embodiment, the enrichment step is used to enrich for amplified adapter-fragment constructs derived from original dsDNA fragments less than about 150 bp, less than about 140 bp, less than about 130 bp, less than about 120 bp, less than about 110 bp, less than about 100 bp, less than about 90 bp, less than about 80 bp, less than about 70 bp, or less than about 60 bp in length are enriched. In another embodiment, the enrichment step is used to enrich for amplified adapter-fragment constructs derived from original dsDNA fragments from about 40 bp to about 150 bp in length, from about 60 bp to about 140 bp, from about 70 bp to about 130 bp, or from about 80 bp to about 120 bp in length are enriched. In general, any known means in the art can be used to enrich dsDNA fragments. For example, size selection can be performed before the library preparation (i.e., cfDNA input size selection) or during the library preparation. In general, any known means in the art can be used to enrich dsDNA fragments. For example, the size selection can be achieved using size selection beads, for example, solid phase reversible immobilization (SPRI) beads (AMPure XP size selection beads, New England BioLabs, Ipswich, MA), or a gel-electrophoresis based method. In another embodiment, a post library preparation clean-up step, e.g., using a PCR cleanup or bead based clean-up (e.g., SPRI beads) can also be removed to remove adapter-fragment constructs derived from dsDNA fragments above a desired cut off length (e.g., derived from dsDNA fragments>150 bp). In one embodiment, at step 535, the sequencing library is considered to be enriched for adapter-fragment constructs derived from fragments less than about 150 bp in length when the proportion of adapter-fragment constructs derived from fragments less than 150 bp in length is higher compared to a sequencing library prepared without a size based enrichment step. In another embodiment, after enrichment, adapter-fragment constructs derived from dsDNA fragments below a size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample.

Figure 6A:
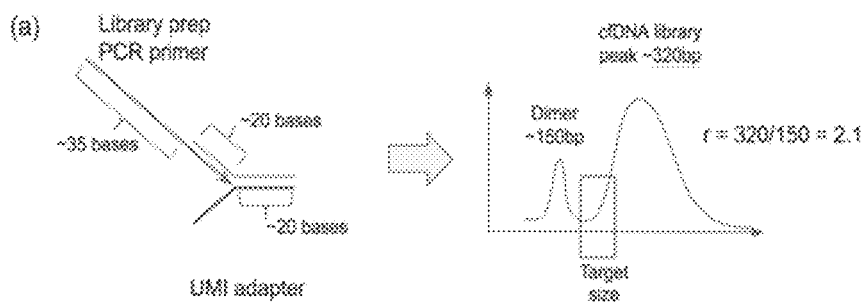
FIG. 6A illustrates a library preparation using conventional full-length primers.

As is well known in the art, cell-free DNA fragments obtained from a plasma sample typically have a fragment length distribution with a peak of about 170 bp. As shown in FIG. 6A, in a conventional library preparation procedure, 40 bp adapters are ligated to both ends of the dsDNA fragments and 55 bp amplification primers (i.e., PCR primers) having a 20 bp 3'-end are used in amplification of the adapter-fragment constructs. Accordingly, the amplified adapter-fragment constructs in conventional library preparation have a peak length distribution of about 320 bp (170 bp fragment+40 bp adapter (×2)+35 bp non-overlapping primer region (×2)). Adapter dimers from conventional library preparation procedure, after amplification with PCR primers, are 150 bp in length (40 bp adapter (×2)+35 bp non-overlapping primer region (×2)). As such, the size difference is only 140 bp between library (320 bp) and dimers (150 bp), giving a size differential ratio of only 2.1 (i.e., 320 bp/150 bp=2.1), which results in poor discrimination between adapter dimers and amplified adapter-fragments constructs during subsequent enrichment and/or cleanup steps.

Figure 6B:
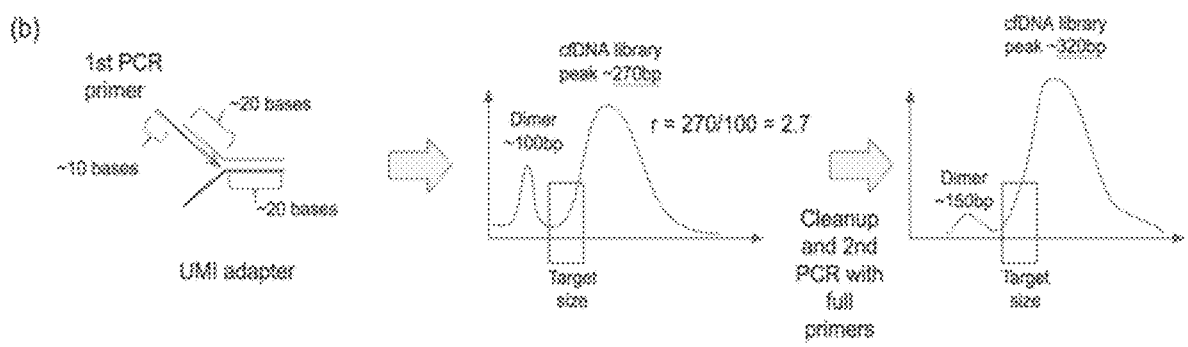
FIG. 6B illustrates a library preparation and enrichment strategy in accordance with the embodiment described in conjunction with FIG. 5.

As shown in FIG. 6B, 40 bp dsDNA adapters can be ligated to both ends of a 170 bp fragment from a test sample, generating a 250 bp dsDNA adapter-fragment construct, and the 250 bp construct amplified using a set of 30 bp first primers comprising a 20 bp complementary 3'-end and a 10 bp free 5'-end, thereby generating amplified adapter-fragment constructs comprising 270 bp. Adapter dimers from conventional library preparation procedure, after amplification with PCR primers, are 100 bp in length (see FIG. 6B). Although, the size difference is only 140 bp between library (270 bp) and dimers (100 bp), the use of shorter primers (i.e., 30 bp versus 55 bp) results in an increased size differential ratio of 2.7 (i.e., 270 bp/100 bp=2.7), which results in improved discrimination between adapter dimers and amplified adapter-fragments constructs during subsequent enrichment and/or cleanup steps. In the case of shorter original dsDNA fragments, for example, original fragments of 140 bp, results in an increased size differential of 2.4 (i.e., 240 bp/100 bp=2.4, versus 290 bp/150 bp=1.93 using conventional library preparation adapters (40 bp) and primers (75 bp)), and thus, an improved ability to discriminate between adapter dimers and amplified adapter-fragments constructs during subsequent enrichment and/or cleanup steps. Similarly, original fragments of 100 bp, results in an increased size differential of 2 (i.e., 200 bp/100 bp=2, versus 250 bp/150 bp=1.67 using conventional library preparation adapters (40 bp) and primers (having 35 bp free 5'-end)), and thus, an improved ability to discriminate between adapter dimers and amplified adapter-fragments constructs during subsequent enrichment and/or cleanup steps.

Optionally, at step 530 the enriched adapter-fragment constructs are amplified using a second set of primers in a second amplification or extension reaction (e.g., a PCR reaction) to generate an enriched sequencing library. For example, the enriched adapter-fragment constructs may be amplified in a PCR reaction using a DNA polymerase, a plurality of dNTPs, and a second set of primers. In one embodiment, the second set of primers may include one or more sequencing oligonucleotides for use in subsequent cluster generation and/or sequencing (e.g., known P5 and P7 sequences for used in sequencing by synthesis (SBS) (Illumina, San Diego, CA)). In some embodiments, enrichment step 525 reduces the amount of adapter dimers relative to the adapter-fragments constructs. Optional amplification step 530 in the enriched sample results in further amplification of the enriched adapter-fragment constructs, but not the adapter dimers (which are largely removed from the reaction through the enrichment step), thereby further enriching adapter-fragments constructs relative to adapter dimers.

After library preparation, the sequencing library can be sequenced to obtain sequence data or sequence reads and the sequence data or reads analyzed. In one embodiment, the sequence data or reads can be analyzed for use in detecting cancer, screening for cancer, determining cancer stage or status, monitoring cancer progression and/or classifying cancer (not shown).

Figure 7:
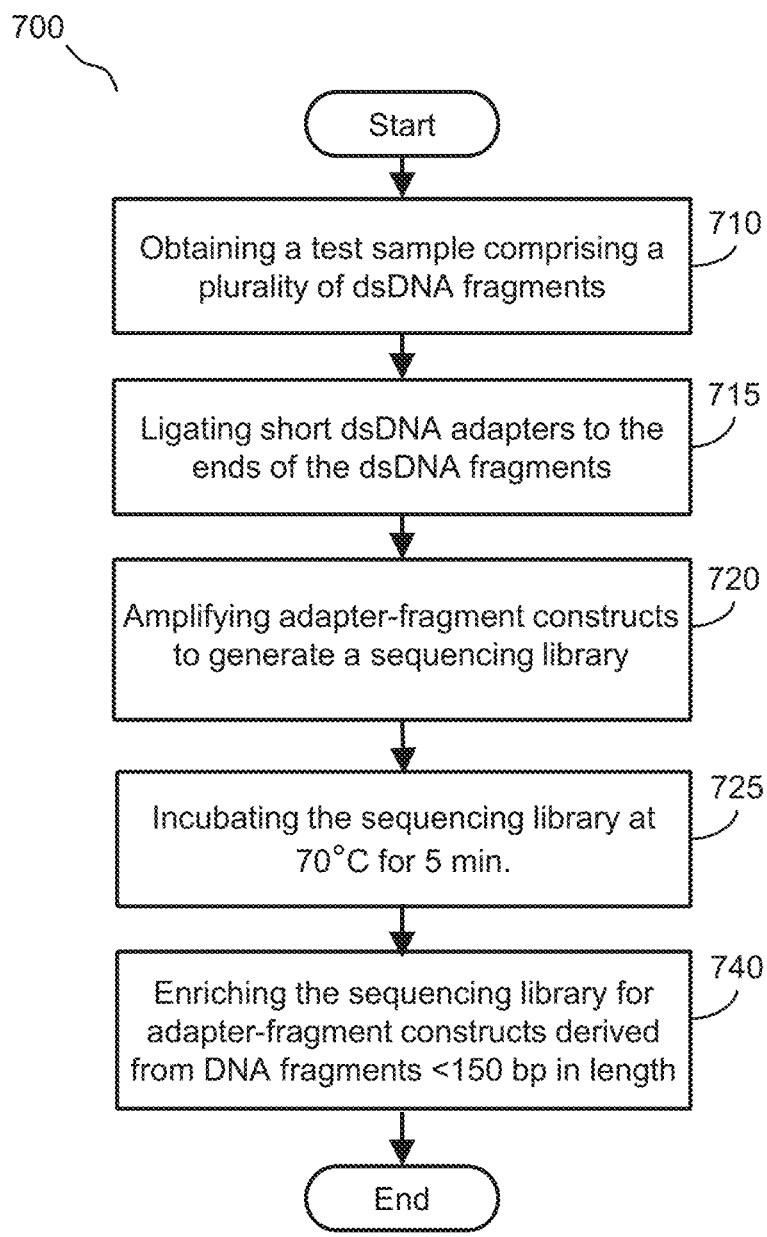
FIG. 7 is a flow diagram illustrating a method for preparing an enriched sequencing library using UMI-free adapters, in accordance with another embodiment of the present invention.

FIG. 7 is a flow diagram illustrating a method 700 for preparing an enriched sequencing library from a test sample comprising a plurality of double-stranded DNA (dsDNA) fragments. As shown in FIG. 7, at step 710, a test sample (e.g., a biological test sample) is obtained from a subject (e.g., a patient). As noted above, the test sample may be a biological test sample selected from the group consisting of blood, whole blood, a blood fraction, plasma, serum, urine, fecal, saliva, a tissue biopsy, pleural fluid, pericardial fluid, cerebral spinal fluid, peritoneal fluid sample, and any combination thereof. In certain aspects, the test sample or biological test sample comprises a plurality of cell-free nucleic acids (e.g., cell-free DNA (cfDNA) and/or cell-free RNA (cfRNA)) fragments. In certain embodiments, the test sample or biological test sample comprises a plurality of cell-free nucleic acids (e.g., cell-free DNA and RNA) fragments originating from healthy cells and from cancer cells. In some embodiments, the test sample comprises a plurality of circulating tumor DNA (ctDNA). In one embodiment, cell-free nucleic acids (e.g., cfDNA and/or cfRNA) can be extracted and/or purified from the test sample (using a commercially available kit, as noted above) before proceeding with subsequent library preparation steps.

At step 715 double-strand DNA adapters are ligated to the dsDNA molecules obtained from step 710 in a ligation reaction to generate a plurality of dsDNA adapter-fragment constructs. The ligation reaction can be performed using any suitable ligation step (e.g., using a ligase) which joins the dsDNA adapters to the dsDNA fragments to form dsDNA adapter-fragment constructs. In one example, the ligation reaction is performed using T4 DNA ligase. In another example, T7 DNA ligase is used for adapter ligation to the modified nucleic acid molecule. As described above, the ends of the dsDNA molecules may be repaired, phosphorylated and/or end-tailed prior to ligation of adapters to the ends of the dsDNA molecules.

In one embodiment, the adapter comprises a short dsDNA oligonucleotide. For example, the adapters used in the practice of the invention may be less than 40 bp, less than 30 bp, less than 25 bp, or less than 20 bp in length. In conventional library preparation, typically adapters ligated to dsDNA fragments are at least 40 bp in length and comprise a unique molecular identifier (UMI) sequence, a universal primer and/or one or more sequencing oligonucleotides for use in subsequent cluster generation and/or sequencing (e.g., known P5 and P7 sequences for used in sequencing by synthesis (SBS) (Illumina, San Diego, CA)). However, the use of shorter adapters does not allow for all of these elements to be included in the adapter. In one embodiment, the adapters ligated to the dsDNA fragments do not include a unique molecular identifier (UMI) sequence. In another embodiment, the adapters ligated to the dsDNA fragments only include a very short UMI sequence, for example 4 bp or less in length. In still another embodiment, the adapters consist essentially of only a universal primer for subsequent amplification of the fragments.

In accordance with the present invention, as shown in step 720, the sample from step 715 is enriched for adapter-fragment constructs derived from nucleic acids (dsDNA fragments) below a size threshold (e.g., less than about 150 bp, less than about 140 bp, less than about 120 bp, or less than about 100 bp in length) using a size selection step. In one embodiment, adapter-fragment constructs derived from dsDNA fragments less than about 150 bp, less than about 140 bp, less than about 130 bp, less than about 120 bp, less than about 110 bp, less than about 100 bp, less than about 90 bp, less than about 80 bp, less than about 70 bp, or less than about 60 bp in length are enriched. In another embodiment, adapter-fragment constructs derived from dsDNA fragments from about 40 bp to about 150 bp in length, from about 60 bp to about 140 bp, from about 70 bp to about 130 bp, or from about 80 bp to about 120 bp, are enriched. In general, any known means in the art can be used to enrich dsDNA fragments. For example, size selection can be performed before the library preparation (i.e., cfDNA input size selection) or during the library preparation. In general, any known means in the art can be used to enrich dsDNA fragments. For example, the size selection can be achieved using size selection beads, for example, solid phase reversible immobilization (SPRI) beads (AMPure XP size selection beads, New England BioLabs, Ipswich, MA), or a gel-electrophoresis based method. In another embodiment, a post library preparation clean-up step, e.g., using a PCR cleanup or bead based clean up (e.g., SPRI beads) can also be utilized to remove adapter-fragment constructs derived from dsDNA fragments above a desired cut off length (e.g., derived from dsDNA fragments>150 bp). In one embodiment, the present invention further includes an incubation step to denature adapter dimers prior to the enrichment step. For example, the adapter-fragment construct sample obtained from step 715 can be incubated at from about 45° C. to about 70° C. for from about 2 min to about 60 min to denature adapter dimers prior to enrichment. In some embodiments, the incubated may be from about 55° C. to about 70° C. In other embodiments, the incubation may be from about 2 min to about 50 min, from about 3 min to about 30 min, or from about 5 min to about 20 min, to denature adapter dimers prior to enrichment. In one embodiment, the incubation is sufficient to denature any adapter dimers, but does not denature longer adapter-fragment constructs. Accordingly, enrichment procedures specific for dsDNA molecules can be used to selectively enrich for adapter-fragment constructs, and thereby eliminating or reducing denatured ssDNA adapters. For example, a bead based enrichment procedure, specific for dsDNA molecules, may be used to enrich for adapter-fragment constructs over contaminating adapter dimers. In one embodiment, at step 740, the sequencing library is considered to be enriched for adapter-fragment constructs derived from fragments less than about 150 bp in length when the proportion of adapter-fragment constructs derived from fragments less than 150 bp in length is higher compared to a sequencing library prepared without a size based enrichment step. In another embodiment, after enrichment, adapter-fragment constructs derived from dsDNA fragments below a size threshold (e.g., less than about 150 bp, less than about 140 bp, less than about 120 bp, or less than about 100 bp in length) comprise more than 25%, more than 30%, more than 40%, or more than 50% of the dsDNA molecules in the test sample.

Optionally, at step 725 the enriched adapter-fragment constructs obtained from step 720 are amplified to generate a sequencing library. For example, the adapter-fragment constructs may be amplified by PCR using a DNA polymerase, a plurality of dNTPs, and a set of amplification primers. In one embodiment, the set of amplification primers utilized may include unique molecular identifiers (UMIs), a universal primer and/or one or more sequencing oligonucleotides for use in subsequent cluster generation and/or sequencing (e.g., known P5 and P7 sequences for used in sequencing by synthesis (SBS) (Illumina, San Diego, CA)).

After library preparation, the sequencing library can be sequenced to obtain sequence data or sequence reads and the sequence data or reads analyzed. In one embodiment, the sequence data or reads can be analyzed for use in detecting cancer, screening for cancer, determining cancer stage or status, monitoring cancer progression and/or classifying cancer (not shown).

Figure 8:
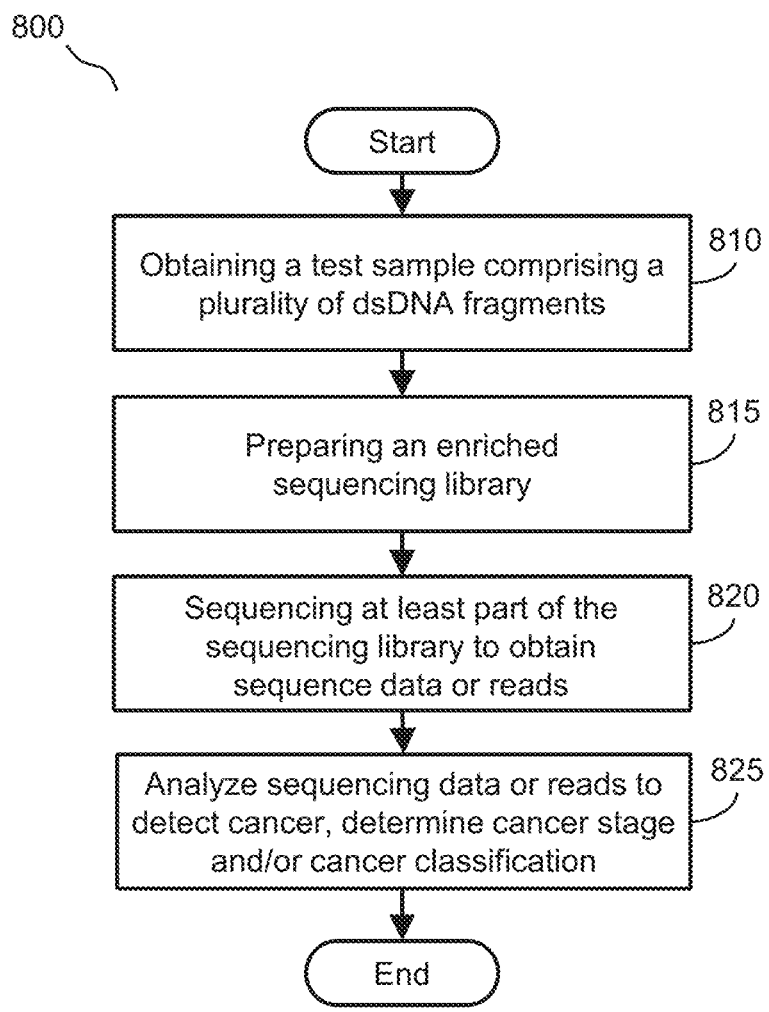
FIG. 8 is a flow diagram illustrating a method for detecting cancer, screening for cancer, determining cancer status, monitoring cancer progression, and/or determining a cancer classification, in accordance with the present invention.

FIG. 8 is a flow diagram illustrating a method 800 for preparing an enriched sequencing library from a cell-free DNA test sample for use thereof in detecting cancer, determining cancer status, monitoring cancer progression, and/or determining a cancer classification.

As shown in FIG. 8, at step 810, a test sample (e.g., a biological test sample) is obtained from a subject (e.g., a patient) known to have or suspected of having cancer. In one embodiment, the test sample may be a biological test sample selected from the group consisting of blood, plasma, serum, urine, fecal, saliva samples, and any combination thereof. In other embodiments, the sample is a plasma sample from a cancer patient, or a patient suspected of having cancer. Alternatively, as noted above, the tests sample or biological test sample may comprise a sample selected from the group consisting of whole blood, a blood fraction, a tissue biopsy, pleural fluid, pericardial fluid, cerebral spinal fluid, peritoneal fluid, and any combination thereof. In accordance with some embodiments, the test sample or biological test sample comprises a plurality of cell-free nucleic acids (e.g., cell-free DNA (cfDNA) or cell-free RNA (cfRNA)) fragments. In other embodiments, the test sample or biological test sample comprises a plurality of cell-free nucleic acids (e.g., cell-free DNA and RNA) fragments originating from healthy cells and from cancer cells. Optionally, in one embodiment, cell-free nucleic acids (e.g., cfDNA or cfRNA) can be extracted and/or purified from the test sample or biological test sample before proceeding with subsequent library preparation steps. In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (Qiagen).

At step 815 the cell-free nucleic acid sample (e.g., cfDNA) is used to prepare an enriched sequencing library. As noted above, in accordance with the present invention, the present method includes an enrichment step, either prior to, or during library preparation. For example, in one embodiment, the method comprises enriching a test sample for fragments shorter than 150 bp in length prior to library preparation (as described above in conjunction with FIG. 2). In another embodiment, the method comprises amplification of adapter-fragment constructs in the presence of a blocker to limit amplification of adapter dimers (as described above in conjunction with FIG. 3). In still another embodiment, the method comprises an amplification step using a first set of primers less than 40 bp in length allowing for improved discrimination between adapter dimers and amplified adapter-fragments constructs during subsequent enrichment and/or cleanup steps (as described above in conjunction with FIG. 5).

In one embodiment, the sequencing adapters utilized may include a unique molecular identifier (UMI) sequence, such that, after library preparation, the sequencing library will include UMI tagged amplicons derived from cell-free nucleic acid fragments. In one embodiment, as described in further detail elsewhere herein, unique sequence tags (e.g., unique molecular identifiers (UMIs)) can be used to identify unique nucleic acid sequences from a cell-free nucleic acid sample. For example, differing unique sequence tags (UMIs) can be used to differentiate various unique nucleic acid sequence fragments originating from the test sample. In another embodiment, unique sequence tags (UMIs) can be used to reduce amplification bias, which is the asymmetric amplification of different targets due to differences in nucleic acid composition (e.g., high GC content). The unique sequence tags (UMIs) can also be used to discriminate between nucleic acid mutations that arise during amplification. The unique sequence tags can be present in a multi-functional nucleic acid adapter, which adapter can comprise a unique sequence tag and/or a universal priming site. In another embodiment, the sequencing adapters utilized may include a universal primer and/or one or more sequencing oligonucleotides for use in subsequent cluster generation and/or sequencing (e.g., known P5 and P7 sequences for used in sequencing by synthesis (SBS) (Illumina, San Diego, CA)).

At step 820 at least a portion of enriched sequence library is sequenced to obtain sequencing data or sequence reads, and the sequencing data or sequence reads analyzed. In general, any method known in the art can be used to obtain sequence data or sequence reads from a test sample. For example, in one embodiment, sequencing data or sequence reads from the cell-free DNA sample can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing.

At step 825, the sequencing data or sequence reads can be analyzed for detecting the presence or absence of cancer, screening for cancer, determining cancer stage or status, monitoring cancer progression, and/or for determining a cancer classification (e.g., cancer type or cancer tissue of origin). In another embodiment, the sequencing data or reads can be used to infer the presence or absence of cancer, cancer status and/or a cancer classification. For example, the sequencing data or sequencing reads can be analyzed to identify methylation profiles indicative of the presence or absence of cancer (see, e.g., PCT Application No. PCT/AU2013/001088, filed Sep. 20, 2013, now WO 2014/043763 A1) or to identify one or more mutational signatures indicative of the presence or absence of cancer (see, e.g., PCT Application No. PCT/US2017/060472, filed Nov. 7, 2017). In other embodiments, the sequence data or sequence reads can be analyzed to assess the fractional contribution of different tissues to a DNA mixture (e.g., for assessment of a cancer tissue of origin) as described in PCT Application No. PCT/CN2015/084442, filed Jul. 20, 2015, now WO 2016/008451. Alternatively, the sequencing data or sequencing reads can be utilized to analyze nucleic acid fragmentation patterns for the detection and/or classification of cancer (e.g., cancer tissue of origin) as described in PCT Application No. PCT/CN2016/091531, filed Jul. 25, 2016, now WO 2017/012592.

In one embodiment, the sequencing data or sequence reads can be analyzed to detect the presence or absence of, screening for, determine the stage or status of, monitor progression of, and/or classify a carcinoma, a sarcoma, a myeloma, a leukemia, a lymphoma, a blastoma, a germ cell tumor, or any combination thereof. In some embodiments, the carcinoma may be an adenocarcinoma. In other embodiments, the carcinoma may be a squamous cell carcinoma. In still other embodiments, the carcinoma is selected from the group consisting of: small cell lung cancer, non-small-cell lung, nasopharyngeal, colorectal, anal, liver, urinary bladder, cervical, testicular, ovarian, gastric, esophageal, head-and-neck, pancreatic, prostate, renal, thyroid, melanoma, and breast carcinoma. In another embodiment, the sequencing data or sequence reads can be analyzed to detect presence or absence of, screening for, determine the stage or status of, monitor progression of, and/or classify a sarcoma. In certain embodiments, the sarcoma can be selected from the group consisting of: osteosarcoma, chondrasarcoma, leiomyosarcoma, rhabdomyosarcoma, mesothelial sarcoma (mesothelioma), fibrosarcoma, angiosarcoma, liposarcoma, glioma, and astrocytoma. In still another embodiment, the sequencing data or sequence reads can be analyzed to detect presence or absence of, screening for, determine the stage or status of, monitor progression of, and/or classify leukemia. In certain embodiments, the leukemia can be selected from the group consisting of: myelogenous, granulocytic, lymphatic, lymphocytic, and lymphoblastic leukemia. In still another embodiment, the sequencing data or sequence reads can be used to detect presence or absence of, screening for, determine the stage or status of, monitor progression of, and/or classify a lymphoma. In certain embodiments, the lymphoma can be selected from the group consisting of: Hodgkin's lymphoma and Non-Hodgkin's lymphoma.

Sequencing and Bioinformatics

Aspects of the invention include sequencing of nucleic acid molecules to generate a plurality of sequence reads, and bioinformatic manipulation of the sequence reads to carry out the subject methods.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslavsky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in U.S. Patent Application Publication No. 2009/0026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).

Biological Samples

Aspects of the invention involve obtaining a sample, e.g., a biological sample, such as a tissue and/or body fluid sample, from a subject for purposes of analyzing a plurality of nucleic acids (e.g., a plurality of cfDNA molecules) therein. Samples in accordance with embodiments of the invention can be collected in any clinically-acceptable manner. Any sample suspected of containing a plurality of nucleic acids can be used in conjunction with the methods of the present invention. In some embodiments, a sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a sample can comprise a fine needle aspirate or biopsied tissue. In some embodiments, a sample can comprise media containing cells or biological material. In some embodiments, a sample can comprise a blood clot, for example, a blood clot that has been obtained from whole blood after the serum has been removed. In some embodiments, a sample can comprise stool. In one preferred embodiment, a sample is drawn whole blood. In one aspect, only a portion of a whole blood sample is used, such as plasma, red blood cells, white blood cells, and platelets. In some embodiments, a sample is separated into two or more component parts in conjunction with the present methods. For example, in some embodiments, a whole blood sample is separated into plasma, red blood cell, white blood cell, and platelet components.

In some embodiments, a sample includes a plurality of nucleic acids not only from the subject from which the sample was taken, but also from one or more other organisms, such as viral DNA/RNA that is present within the subject at the time of sampling.

Nucleic acid can be extracted from a sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cfDNA) is extracted from a sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor DNA (ctDNA) constitutes a minority population of cfDNA, in some cases, varying up to about 50%. In some embodiments, ctDNA varies depending on tumor stage and tumor type. In some embodiments, ctDNA varies from about 0.001% up to about 30%, such as about 0.01% up to about 20%, such as about 0.01% up to about 10%. The covariates of ctDNA are not fully understood, but appear to be positively correlated with tumor type, tumor size, and tumor stage. E.g., Bettegowda et al., Sci Trans Med, 2014; Newman et al., Nat Med, 2014. Despite the challenges associated with the low population of ctDNA in cfDNA, tumor variants have been identified in ctDNA across a wide span of cancers. E.g., Bettegowda et al., Sci Trans Med, 2014. Furthermore, analysis of cfDNA versus tumor biopsy is less invasive, and methods for analyzing, such as sequencing, enable the identification of sub-clonal heterogeneity. Analysis of cfDNA has also been shown to provide for more uniform genome-wide sequencing coverage as compared to tumor tissue biopsies. In some embodiments, a plurality of cfDNA is extracted from a sample in a manner that reduces or eliminates co-mingling of cfDNA and genomic DNA. For example, in some embodiments, a sample is processed to isolate a plurality of the cfDNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, New Jersey), or in collection tubes that are adapted for isolation of cfDNA (for example, the CELL FREE DNA BCT® family of products from Streck, Inc., Omaha, Nebraska) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA.

Plasma DNA can be extracted using any suitable technique. For example, in some embodiments, plasma DNA can be extracted using one or more commercially available assays, for example, the QIAmp Circulating Nucleic Acid Kit family of products (Qiagen N.V., Venlo Netherlands). In certain embodiments, the following modified elution strategy may be used. DNA may be extracted using, e.g., a QIAmp Circulating Nucleic Acid Kit, following the manufacturer's instructions (maximum amount of plasma allowed per column is 5 mL). If cfDNA is being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA yield. First, DNA can be eluted using 30 µL of buffer AVE for each column. A minimal amount of buffer necessary to completely cover the membrane can be used in the elution in order to increase cfDNA concentration. By decreasing dilution with a small amount of buffer, downstream desiccation of samples can be avoided to prevent melting of double stranded DNA or material loss. Subsequently, about 30 µL of buffer for each column can be eluted. In some embodiments, a second elution may be used to increase DNA yield.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy subjects, and a fourth database can contain data from sick subjects with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A method for preparing an enriched sequencing library, the method comprising:
   (a) obtaining a test sample comprising a plurality of double-stranded deoxyribonucleic acid (dsDNA) fragments;
   (b) ligating double-stranded DNA (dsDNA) adapters to both ends of the plurality of dsDNA fragments to generate a plurality of adapter-fragment constructs, wherein each of the dsDNA adapters comprises a first strand and a second strand;
   (c) amplifying the plurality of adapter-fragment constructs to generate a sequencing library, wherein the plurality of adapter-fragment constructs are amplified in the presence of a blocker, the blocker comprising an oligonucleotide sequence having sequence complementarity with at least a portion of the 5'-end of the first strand and at least a portion of the 3'-end of the second strand of the dsDNA adapters; and
   (d) enriching the sequencing library for adapter-fragment constructs derived from the plurality of dsDNA fragments less than about 150 bp in length to generate an enriched sequencing library.

2. The method according to claim 1, wherein the test sample comprises a plurality of dsDNA fragments synthesized from single-stranded ribonucleic acid (ssRNA) molecules, wherein synthesizing the plurality of dsDNA fragments from ssRNA molecules comprises:
   (a) obtaining a test sample comprising a plurality of single-stranded ribonucleic acid (ssRNA) molecules;
   (b) adding an RNA primer to the test sample comprising the plurality of ssRNA molecules to generate a reaction mixture and extending the RNA primer in a first nucleic acid extension reaction using reverse transcriptase to generate a plurality of complementary DNA (cDNA) sequences, wherein the plurality of cDNA sequences are complementary to the plurality of ssRNA molecules; and
   (c) adding one or more DNA primers to the reaction mixture and extending the one or more DNA primers in a second nucleic acid extension reaction using a DNA polymerase to generate a plurality of dsDNA fragments.

3. The method according to claim 1, wherein the plurality of dsDNA fragments comprise cell-free DNA (cfDNA) fragments.

4. The method according to claim 1, wherein the test sample comprises whole blood, a blood fraction, plasma, serum, urine, fecal matter, saliva, a tissue biopsy, pleural fluid, pericardial fluid, cerebrospinal fluid, peritoneal fluid, or any combination thereof.

5. The method according to claim 1, wherein more than 25% of the plurality of dsDNA fragments in the test sample are less than 150 bp in length, prior to the amplifying.

6. The method according to claim 1, wherein the test sample comprises a plasma sample obtained from a patient known to have, or suspected of having cancer.

7. The method according to claim 6, wherein the test sample comprises nucleic acids originating from healthy cells and from cancer cells.

8. The method according to claim 1, wherein the plurality of dsDNA fragments are purified from the test sample, prior to preparing the enriched sequencing library.

9. The method according to claim 1, wherein the plurality of dsDNA fragments in the test sample or the plurality of adapter-fragment constructs derived from the plurality of dsDNA fragments in the test sample are enriched for dsDNA fragments or adapter-fragment constructs derived from the plurality of dsDNA fragments less than 150 bp in length using gel electrophoresis or size selection beads.

10. The method according to claim 9, wherein the size selection beads are utilized to enrich for dsDNA fragments, or adapter-fragment constructs derived from the plurality of dsDNA fragments, having a length of less than 140 bp.

11. The method according to claim 9, wherein the size selection beads are utilized to enrich for dsDNA fragments, or adapter-fragment constructs derived from the plurality of dsDNA fragments, having a length that ranges from 60 bp to 140 bp.

12. The method according to claim 1, wherein the enriched sequencing library is sequenced to generate a plurality of sequence reads.

13. The method according to claim 12, wherein the plurality of sequence reads are identified based on alignment of the plurality of sequence reads to a reference genome, or a portion of a reference genome, or based on a de novo assembly.

14. The method according to claim 12, wherein the plurality of sequence reads are used for detecting cancer, screening for cancer, determining cancer stage or status, monitoring cancer progression, and/or determining a cancer classification.

15. The method according to a claim 14, wherein the cancer classification comprises determining cancer type and/or cancer tissue of origin.

16. The method according to claim 14, wherein the cancer comprises a carcinoma, a sarcoma, a myeloma, a leukemia, a lymphoma, a blastoma, a germ cell tumor, or any combination thereof.

17. The method according to claim 16, wherein the cancer is selected from the group consisting of: adenocarcinoma, squamous cell carcinoma, small cell lung cancer, non-small-cell lung, nasopharyngeal, colorectal, anal, liver, urinary bladder, cervical, testicular, ovarian, gastric, esophageal, head-and-neck, pancreatic, prostate, renal, thyroid, melanoma, breast carcinoma, osteosarcoma, chondrosarcoma, leiomyosarcoma, rhabdomyosarcoma, mesothelial sarcoma (mesothelioma), fibrosarcoma, angiosarcoma, liposarcoma, glioma, astrocytoma, myelogenous, granulocytic, lymphatic, lymphocytic, lymphoblastic leukemia, Hodgkin's lymphoma, Non-Hodgkin's lymphoma, or any combination thereof.

* * * * *